(12) United States Patent
Mathewson

(10) Patent No.: US 7,473,236 B1
(45) Date of Patent: Jan. 6, 2009

(54) VARIABLY ADJUSTABLE BI-DIRECTIONAL DEROTATION BRACING SYSTEM

(76) Inventor: Paul R. Mathewson, 7726 N. Buckboard Dr., Park City, UT (US) 84098

(*) Notice: Subject to any disclaimer, the term of this patent is extended or adjusted under 35 U.S.C. 154(b) by 1826 days.

(21) Appl. No.: 09/664,462

(22) Filed: Sep. 18, 2000

Related U.S. Application Data

(63) Continuation-in-part of application No. 09/004,010, filed on Jan. 7, 1998, now Pat. No. 6,142,965.

(60) Provisional application No. 60/039,104, filed on Feb. 25, 1997.

(51) Int. Cl.
*A61F 13/00* (2006.01)
(52) U.S. Cl. .............. 602/62; 602/23; 602/26; 602/60
(58) Field of Classification Search ............. 602/60–65, 602/20, 23, 26
See application file for complete search history.

(56) References Cited

U.S. PATENT DOCUMENTS

| | | | |
|---|---|---|---|
| 366,590 A | 7/1887 | Lubin | |
| 967,585 A | 8/1910 | Teufel | |
| 2,574,873 A | 11/1951 | Jobst | |
| 2,646,796 A | 7/1953 | Scholl | |
| 3,306,288 A | 2/1967 | Rosenfield | |
| 3,307,546 A | 3/1967 | Cherio et al. | |
| 3,419,003 A | 12/1968 | Krauss et al. | |
| 3,504,672 A | 4/1970 | Moon | |
| 3,529,601 A | 9/1970 | Kirkland | |
| 3,680,549 A | 8/1972 | Lehneis et al. | |
| 3,724,457 A | 4/1973 | Klatte | |
| 3,805,781 A * | 4/1974 | Hoey ........................... | 602/75 |
| 3,831,467 A | 8/1974 | Moore | |
| 3,900,199 A | 8/1975 | McGonagle | |
| 4,201,203 A | 5/1980 | Applegate | |
| 4,269,181 A | 5/1981 | Delannoy | |
| 4,353,362 A | 10/1982 | DeMarco | |
| 4,378,009 A | 3/1983 | Rowley et al. | |
| 4,425,912 A | 1/1984 | Harper | |
| 4,503,846 A | 3/1985 | Martin | |
| 4,697,583 A | 10/1987 | Mason et al. | |
| 4,733,656 A | 3/1988 | Marquette | |
| 4,802,466 A | 2/1989 | Meyers et al. | |
| 4,941,462 A * | 7/1990 | Lindberg ..................... | 602/16 |
| 4,986,264 A | 1/1991 | Miller | |

(Continued)

FOREIGN PATENT DOCUMENTS

DE        4013693 A1 *   8/1991

(Continued)

*Primary Examiner*—Michael Brown
(74) *Attorney, Agent, or Firm*—Morriss O'Bryant Compagni

(57) ABSTRACT

A lightweight orthopedic brace having no rigid structural elements is constructed from flexible material and is designed primarily to provide for restriction of rotational movement and translation about the target joint by providing flexible bracing members which wind in a circumferentially spiraling manner about a target joint to provide active resistance to axial rotation and translation in the joint. The embodiments of the invention disclosed here provide improved means for placing the invention on the body about a joint, improved means for attachment of bracing members to bracing member supports and improved means for adjusting the length of bracing member to selectively provide for restriction of rotational movement about the target joint.

19 Claims, 6 Drawing Sheets

U.S. PATENT DOCUMENTS

| | | | |
|---|---|---|---|
| 5,018,514 A | 5/1991 | Grood et al. | |
| 5,277,697 A | 1/1994 | France et al. | |
| 5,277,698 A | 1/1994 | Taylor | |
| 5,288,287 A | 2/1994 | Castillo et al. | |
| 5,336,161 A | 8/1994 | Lengyel | |
| 5,383,845 A * | 1/1995 | Nebolon | 602/26 |
| 5,385,036 A | 1/1995 | Spillane et al. | |
| 5,399,153 A | 3/1995 | Caprio, Jr. et al. | |
| 5,407,421 A | 4/1995 | Goldsmith | |
| 5,412,957 A * | 5/1995 | Bradberry et al. | |
| 5,433,699 A | 7/1995 | Smith, III | |
| 5,437,619 A | 8/1995 | Malewicz et al. | |
| 5,449,338 A | 9/1995 | Trudell | |
| 5,460,599 A | 10/1995 | Davis et al. | |
| 5,462,517 A | 10/1995 | Mann | |
| 5,472,413 A | 12/1995 | Detty | |
| 5,474,524 A | 12/1995 | Carey | |
| 5,490,831 A | 2/1996 | Myers et al. | |
| 5,507,722 A * | 4/1996 | Richardson | 602/62 |
| 5,512,039 A | 4/1996 | White | |
| 5,520,622 A | 5/1996 | Bastyr et al. | |
| 5,520,625 A | 5/1996 | Malewicz | |
| 5,520,627 A | 5/1996 | Malewicz | |
| 5,527,268 A | 6/1996 | Gildersleeve et al. | |
| 5,797,864 A * | 8/1998 | Taylor | 602/26 |
| 5,873,848 A | 2/1999 | Fulkerson | |
| 6,010,474 A * | 1/2000 | Wycoki | 602/23 |
| 6,063,048 A * | 5/2000 | Bodenschatz et al. | 602/62 |
| 6,142,965 A * | 11/2000 | Mathewson | 602/62 |
| 2006/0036205 A1 * | 2/2006 | Bonutti | 602/75 |

FOREIGN PATENT DOCUMENTS

| | | | |
|---|---|---|---|
| EP | 0050769 | * | 9/1981 |
| JP | 8-196562 | | 6/1996 |
| WO | WO 88/01855 | | 3/1988 |
| WO | 94/00082 | | 1/1994 |

* cited by examiner

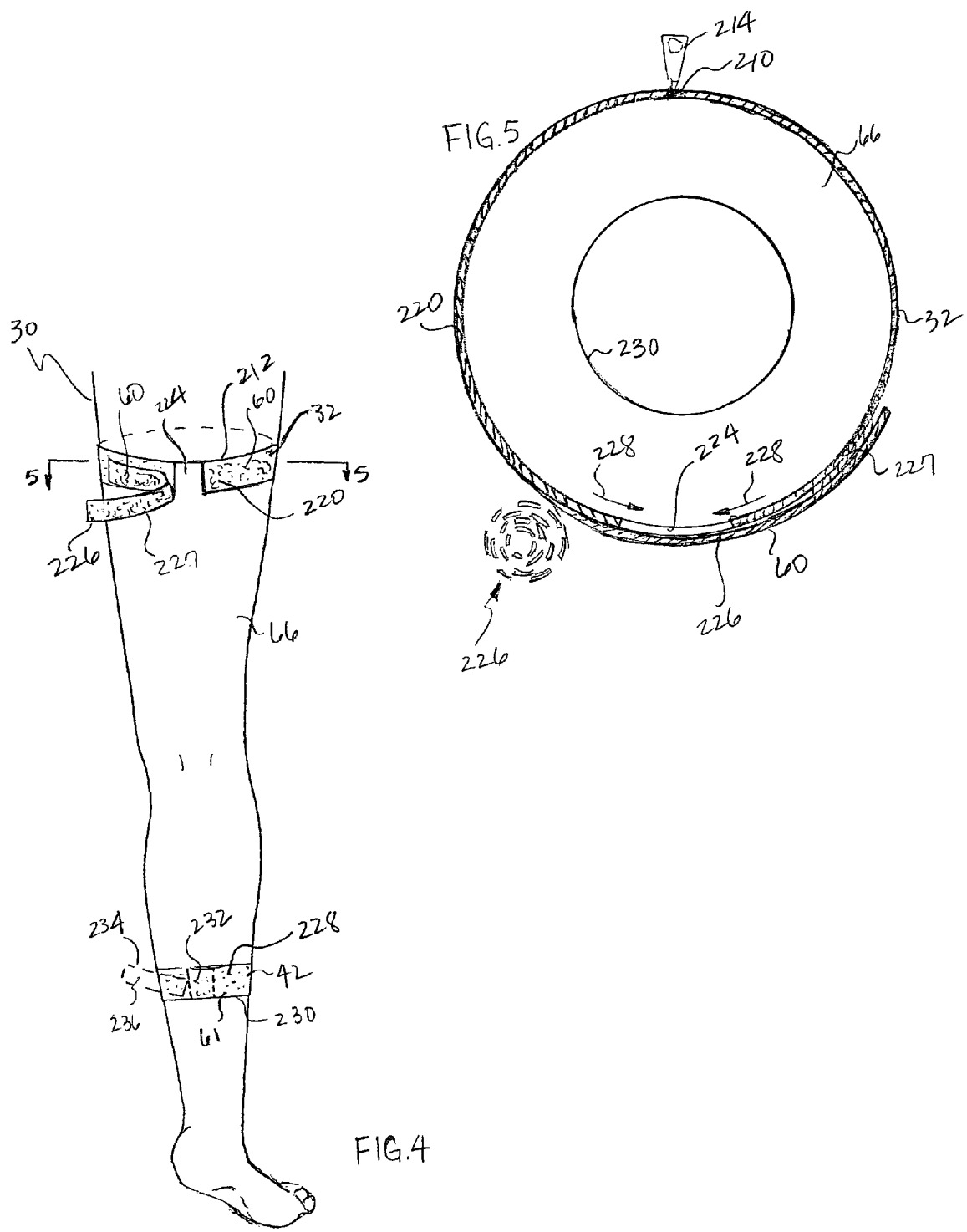

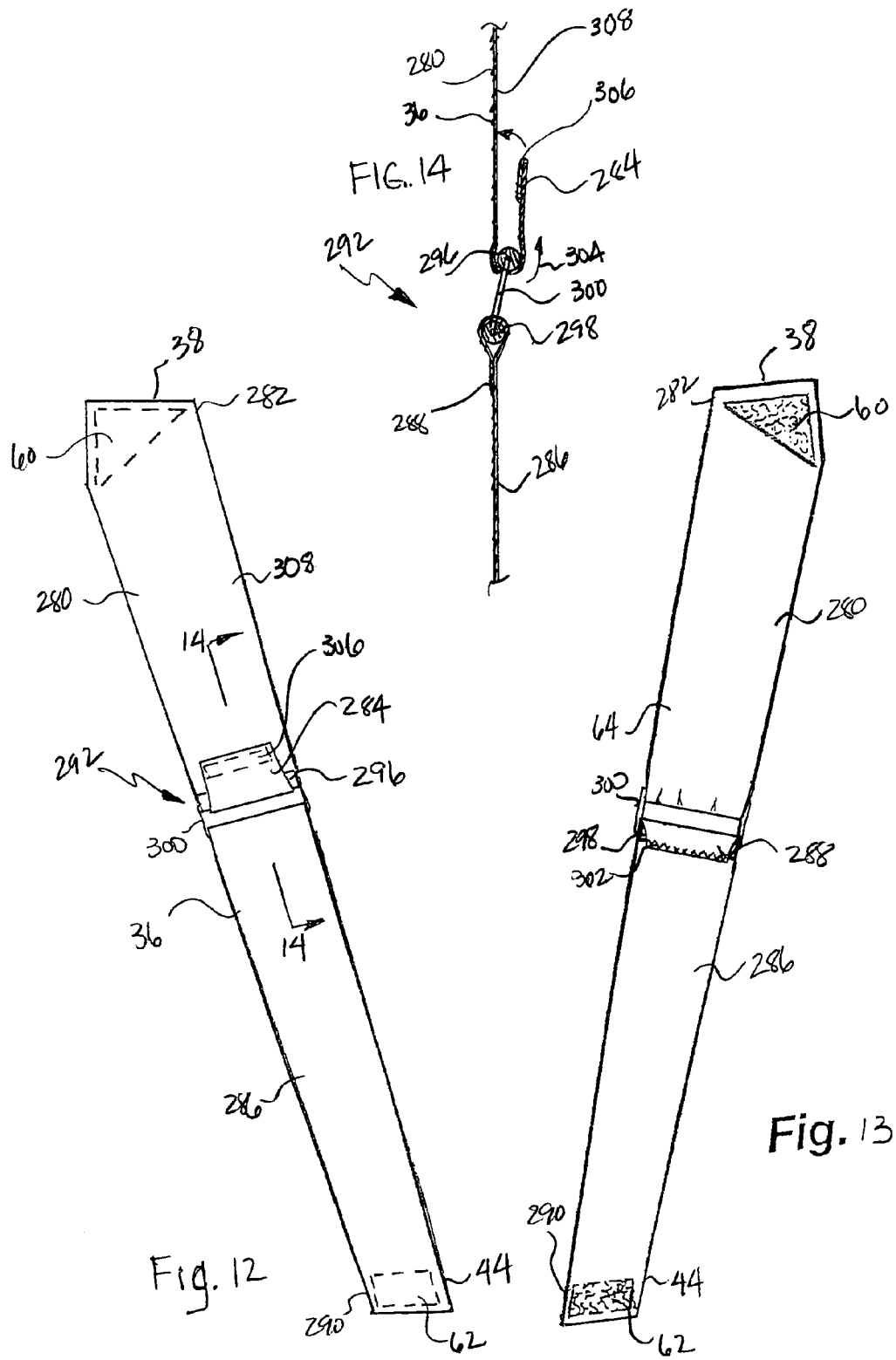

VARIABLY ADJUSTABLE BI-DIRECTIONAL DEROTATION BRACING SYSTEM

CROSS REFERENCE TO RELATED APPLICATIONS

This application is a continuation-in-part application of Ser. No. 09/004,010, filed Jan. 7, 1998 now U.S. Pat. No. 6,142,965, the contents of which are incorporated herein by reference, and further claims the benefit of U.S. provisional application Ser. No. 60/039,104 filed Feb. 25, 1997.

BACKGROUND OF THE INVENTION

1. Field of the Invention

This invention relates generally to an orthopedic support device for physiological joints, and more specifically to an improved non-rigid orthopedic appliance and method for construction of a flexible orthopedic bracing system designed to limit both rotational and translational motion about the joints of human or animal limbs, especially around joints such as the knee.

2. Description of Related Art

Functional bracing of physiological joints, particularly the human knee joint, is a phenomenon of relatively recent origin. Substantial interest and effort in the bracing of knees, in particular, arose in the early 1970's coincident with the origins of "sports medicine." Thus, orthotic bracing systems for various human joints are well known in the art and a wide variety of bracing systems have been developed to address a plethora of conditions for which bracing, in some form, has been thought to be therapeutically beneficial.

The bracing system in widest use over the last ten to fifteen years may be described as comprising a structural frame made up of a plurality of rigid support components which are linked in a dynamic fashion by one or more mechanical hinges. The frame is generally comprised of two sections, designed to attach to the soft tissue areas proximal and distal to the targeted joint, which are themselves joined by a mechanical hinge of varying design to allow the joint to move within the normal plane of motion. As used herein, "proximal" conventionally refers to a point situated toward the wearer's head while "distal" conventionally refers to a point situated away from the wearer's head. These devices may be described as hinge-post-band or hinge-post-shell devices depending on the configuration of the sections attaching to the soft tissue areas. In such examples, the orthotic can be described as a hard mechanical brace.

Hinged orthopedic bracing devices are commonly employed in an effort to provide stability to a skeletal joint which has been weakened by injury or other infirmity. Braces of this type have been designed primarily to help limit joint separation due to hyperextension, or to varus or valgus deformation of the joint. Such devices, as applied to the knee joint, are represented by previously disclosed bracing systems described in U.S. Pat. No. 4,503,846 to Martin, U.S. Pat. No. 4,697,583 to Mason et al., U.S. Pat. No. 4,733,656 to Marquette, U.S. Pat. No. 4,802,466 to Meyers, U.S. Pat. No. 4,941,462 to Lindberg, U.S. Pat. No. 4,986,264 to Miller, U.S. Pat. No. 5,018,514 to Grood, et al., U.S. Pat. No. 5,277,697 to France, at al., U.S. Pat. No. 5,277,698 to Taylor, U.S. Pat. No. 5,336,161 to Lengyel, U.S. Pat. No. 5,433,699 to Smith, U.S. Pat. No. 5,460,599 to Davis, U.S. Pat. No. 5,490,831 to Myers, et al. and U.S. Pat. No. 5,527,268 to Gildersleeve, et al. All of these braces disclose bracing systems comprised of rigid structural elements linked by one or more mechanical hinges. Additional devices of similar construction, having structural elements connected by one or more mechanical hinges, have also been disclosed in U.S. Pat. No. 5,520,627 to Malewicz, as applied to the ankle, and in U.S. Pat. No. 5,437,619 to Malewicz, as applied to the elbow. A derotation brace for the wrist was also disclosed by Malewicz in U.S. Pat. No. 5,520,625.

The brace disclosed by Gildersleeve et al. is a current example of the series of braces representing this technology and comprises a hinged orthopedic brace having a frame and one or more pads attached thereto that provide support for the brace when the frame is mounted on the body. The Gildersleeve bracing device, like all similarly constructed rigid braces with mechanical hinges, is designed to stabilize the joint by restricting movement to one plane corresponding, in the case of a knee, to normal flexion and extension and thereby limiting hyperextension of the joint, as well as limiting lateral movement of the joint.

Many braces, constructed in the aforementioned manner, have also claimed to attenuate rotational deformations of the knee in addition to lateral and hyperextensive displacements. Among such disclosures are U.S. Pat. No. 4,503,846; U.S. Pat. No. 4,733,656; U.S. Pat. No. 4,802,466; U.S. Pat. No. 4,986,264 and U.S. Pat. No. 5,018,514. All of the aforementioned references which disclose braces claiming to provide such rotational stability are of the hinge-post-band/shell construction. In all such bracing systems, any rotational stability that may be provided is linked to both the medial-lateral and the anterior-posterior stability afforded by the brace. However, rotational stability is not the primary design feature of these braces, but a presumed consequence stemming from that medial-lateral and anterior-posterior stability which the bracing system may provide. Any such stability depends on the ability of the brace to remain stationary with respect to the body after application of the brace and during its use.

In all such rigid, hinged bracing systems, the stability of the brace on the leg is provided by pliant straps which encircle the leg at specific locations. The straps require considerable tightening about the leg to assure that the relatively heavy and rigid devices stay in place about the knee or leg. Even so, the weight of such devices results in the device migrating downwardly on the leg and any rotational stability that might be provided by such devices is lost. In theory, post-hinge-band/shell-type bracing systems claiming to restrict lateral, rotational and/or hyperextensive movement should be of some value in terms of ameliorating the incidence of joint injuries, but that has not been demonstrated biomechanically. The design of these braces is directed to reducing the likelihood of re-injury resulting primarily from medial/lateral and hyperextensive forces rather than those resulting from rotational forces.

While a significant number of injuries occur as a result of lateral and hyperextensive forces on the knee (as well as other joints), it is recognized that a great many joint injuries, especially those involving the anterior cruciate ligament (ACL) of the knee, result from a torsional rotation force about the joint. Current mechanical hinged braces have, as yet, not demonstrated biomechanical efficacy in helping to prevent injuries resulting from such rotational forces.

Other bracing systems have also been disclosed which are less rigid and/or mechanical, such as that disclosed in U.S. Pat. No. 3,680,549 to Lehneis. Still other bracing systems are disclosed which employ soft materials in an effort to provide some support to a joint. Such devices do not, and are not specifically meant to, limit the movement of a joint under stress and, therefore, are not able to fulfill the role of an orthopedic brace. Such devices are disclosed in U.S. Pat. No. 5,399,153 to Caprio, et al., in U.S. Pat. No. 5,407,421 to Goldsmith, in U.S. Pat. No. 5,462,517 to Mann, in U.S. Pat. No. 5,472,413 to Detty and in U.S. Pat. No. 5,474,524 to Carey, among others. Fabric bandages have also been used as joint supports, as disclosed in U.S. Pat. No. 366,590 to Lubin, U.S. Pat. No. 967,585 to Teufel and U.S. Pat. No. 5,385,036 to Spillane, et al. Those devices are stretchably elastic in all directions and thus are designed only to provide a constant, non-variable level of compression about the affected body area. These devices are not designed to limit joint rotation. Indeed, elastic fabric bandages are not effective at preventing joint rotation under physiologically significant loads because of their elasticity in all dimensions. Thus, they cannot accomplish the objectives for which a true bracing system is designed.

Known bracing systems are not specifically designed to effectively constrain axial rotation about a human or animal joint. Thus, it would be advantageous in the art to provide an orthotic device which is specifically designed to provide substantial restriction of axial rotation, as well as translation, about a physiological joint. Further, it would be advantageous to provide such an axial derotation orthotic with the characteristics of being lightweight and flexible, having no rigid structural components or hinged mechanisms, and providing for comfortable, sustained protection while the wearer engages in normal activity.

BRIEF SUMMARY OF THE INVENTION

In accordance with the present invention, a bracing apparatus is structured to limit axial rotation of an articulating joint by providing a substantially non-rigid, circumferentially spiraling member which exerts resistance to rotation about the longitudinal axis of the joint, thereby limiting axial rotation of the joint while enabling normal flexion and extension through the joint. The present invention may be used in humans and animals alike, and may be adapted for use with virtually any articulating joint which may require the limitation of axial rotation therethrough. However, for simplification of description, the invention is described herein with respect to a human knee joint as merely one exemplar application of the invention.

The present invention is comprised of a substantially non-rigid member which extends over and about a target joint in which derotation is desired and extends from a location proximal to the joint to a position distal to the joint along the longitudinal axis of the joint. The substantially non-rigid member is constructed to provide resistance to rotation about the longitudinal axis of the joint by providing circumferentially spiraling means capable of limiting rotation about the joint while allowing normal flexion and extension of the joint (i.e., rotation through a lateral axis, which is perpendicular to the longitudinal axis of the joint running co-axially with the long axis of the limb or other body structure).

In one exemplar embodiment of the present invention, the bracing apparatus is comprised of at least one circumferentially and spirally windable elongated bracing member and a bracing member support. The elongated bracing member is of sufficient length to allow the bracing member to be wound in a circumferentially spiraling manner about the joint and to extend from a location above the joint to a location below the joint. Bracing members of this invention are substantially non-rigid and are flexible so that they may be wound about the area of the joint. The bracing members, however, are preferably substantially inelastic along a longitudinal axis thereof, meaning from one end of the bracing member to the other end of the bracing member. The bracing members may, most suitably, be elastic in a direction normal to the longitudinal axis of the bracing members to accommodate changes in muscle mass distribution during muscle contraction. Alternatively, the bracing members may be inelastic in a direction normal to the longitudinal axis thereof.

In one presently preferred embodiment, the bracing members of the invention may be elongated bands of material which are sized in length to be circumferentially and spirally wound about the limb, above and below the joint. Suitable materials which may be used in construction of the elongated bands include woven fabrics, non-woven natural or artificial materials, and particularly those which provide elasticity only in a direction normal to the longitudinal axis thereof.

The brace of the present invention may comprise a first bracing member support which is positioned to one side of the joint and the second bracing member support which is positioned to the other side of the joint. For example, the first bracing member support may be positioned about the thigh in a location proximal to (i.e. above) the knee joint and the second bracing member support may be positioned about the calf distal to (i.e. below) the knee joint. The first and second bracing member supports provide a means for attaching the circumferentially spiraling bracing members thereto and are constructed to allow variably adjustable securement of the bracing members thereto to enhance delimited rotation about the joint. The first and second bracing member supports may be continuous collars which are sized to extend about an area of the body (e.g., a limb or digit) in proximity to the joint. The collars are structured to provide a means for releasably attaching the bracing members thereto to readily provide adjustability of the bracing members. Any structure which suitably provides a stable point for adjustably anchoring the bracing members thereto may be employed as bracing member supports. Alternatively, the bracing members may be permanently affixed to the collars in an embodiment where length-adjustability is provided in the bracing members, as described further hereinafter.

The brace of the present invention may alternatively comprise at least one flexible sleeve which is sized to be positioned against the body and about which the circumferentially windable bracing members are positioned. In one disclosed embodiment, the first and second bracing member supports, or collars, may be integrally attached to, or formed with, the flexible sleeve. The sleeve may be configured in a manner to provide adaptability of the sleeve to limbs or joints of different diameter; that is, for example, to adapt the sleeve to the leg of a small person or the leg of a large person. Various means or devices may be employed to render the sleeve adaptable to different sizes of limbs or joints.

In one exemplar embodiment, the sleeve is configured to facilitate placement of the sleeve on a wearer's limb or about a joint by being formed with a closeable opening at or near a terminal end of the sleeve. For example, a zipper opening may be formed beginning at the proximal edge of the sleeve and extending toward the distal edge of the sleeve, enabling the proximal portion of the sleeve to be temporarily enlarged for fitting over the thigh of the wearer, for example. Once positioned about the limb or joint, the zipper may then be closed to secure the sleeve in tight registration against the wearer's body. In addition to the closeable opening, the sleeve may also include connecting devices positioned along the sides of the closeable opening which allow the opposing sides of the opening to be brought into proximity with each other to facilitate closing the opening. Any number of devices may be employed as a closeable opening in the sleeve, a zipper being just one example. In addition, a closeable opening may be employed at either or both terminal ends of the sleeve.

The sleeve may also be formed from material having a coefficient of elasticity which helps shape the sleeve to the wearer's body and keep it in place about the body. Additionally, the sleeve may be configured to ensure that the sleeve stays in place about the limb, particularly around the larger thigh area of a leg, and does not drift downward or roll down the limb. Thus, for example, the sleeve may be formed with a proximal portion and/or a distal portion near the terminal ends of the sleeve which have a lower coefficient of elasticity as compared with the coefficient of elasticity of the sleeve, thereby causing the proximal portion and/or distal portion to substantially fix the circumference of the terminal end or terminal ends of the sleeve to prevent the sleeve from slipping or rolling down the body. As used herein with respect to describing the proximal portion, distal portion or stabilizing straps, "substantially fix" or "substantially fixes" means that the circumferential dimension of the sleeve is not absolutely inelastic, but is capable of exhibiting a small degree of elastic expansion (e.g., less than a ten percent increase in circumferential dimension). The proximal portion may also be formed with stiffener devices which prevent the proximal portion from rolling down upon the sleeve. These adaptations may also be incorporated into the distal portion of the sleeve encircling the distal area of a joint to ensure securement of the sleeve there.

In a particularly suitable embodiment of the invention, the proximal portion partially encircles the sleeve near the proximal edge of the sleeve, thereby providing a portion of higher elasticity material which facilitates placement of the sleeve on the body while providing a portion of material of lower elasticity which substantially fixes the terminal end of the sleeve to the wearer's body. Since the proximal portion may be positioned near the proximal edge of the sleeve and, therefore, may coincide with the placement of the bracing member support, the proximal portion may, in one embodiment, be structured with securement apparatus which allows the bracing members to be secured to the proximal portion in a manner as previously described. Further, a strap may be positioned in proximity to the proximal portion and oriented to be positionable over that portion of the sleeve not covered by the proximal portion. The strap not only completes the encirclement of the proximal portion about the sleeve to fix the circumference thereof, but provides some sizing of the sleeve. The strap may also be structured with securement apparatus to assist in supporting the bracing members thereagainst. The sleeve may be configured with a distal portion of lower elasticity which is sized to partially encircle the sleeve near the distal end thereof, and may be similarly structured to function as previously described with respect to the proximal portion.

A second flexible sleeve may be employed to extend over the bracing members once they are wound about the joint, and may be sized to be essentially co-extensive with the first flexible sleeve. The second flexible sleeve may operate to hold the bracing system in place on the limb and may provide a uniform compressive support system at the same time.

The derotation bracing apparatus of the present invention may be formed on the wearer's body by circumferentially and spirally winding at least one bracing member about the body on either side of the joint. More specifically, the first bracing member support may be positioned to one side of the joint (e.g., placed about the thigh and above the knee), the second bracing member support may be positioned on the other side of the joint (e.g., placed about the calf and below the knee), and the bracing member or bracing members may be initially secured at one end thereof to a bracing member support. The bracing member or members are then circumferentially wound, in a spiraling fashion, about the body (e.g., the leg) and are secured to the other bracing member support. At least one, or a plurality of, bracing members may be circumferentially and spirally wound about the body in the same direction. In a particularly preferred embodiment, however, a first plurality of bracing members are circumferentially and spirally wound about the body in one direction (e.g., levorotatory) and a second plurality of bracing members are circumferentially and spirally wound in the opposite direction (e.g., dextrorotatory) about the body to provide restriction to rotation about the joint in both internal and external directions. As used herein, the direction of turn of "levorotatory" and "dextrorotatory" is determined by the longitudinal axis formed through the target joint and by initiation of turning from the proximal end of the bracing apparatus toward the distal end.

One may envision this restrictive action to rotation about the joint by visualizing the opposing ends of each bracing member as two points, one point fixedly positioned on the surface of the limb above the joint and the other point fixedly positioned on the surface of the limb below the joint. At any given angle of flexion of the joint, the distance between these two points is fixed as long as the joint remains in the single plane defined by "normal" flexion/extension (i.e., a defined plane of motion). For example, a bracing member of substantially fixed or inelastic length, which is wrapped in a circumferentially spiraling orientation around the limb and fully extended in length when the limb is in a normal (i.e. relaxed frontal) orientation, defines a certain distance between the two fixed points on the limb and also defines a certain circumference about the limb in that orientation. As rotational force is applied to the joint (e.g., the femur rotates axially relative to the tibia), the fixed points, either proximal or distal to the joint, move out of the defined single plane of motion and the distance between the two fixed points is increased. The only way that such an increase in the distance between the two fixed points can be accommodated by a substantially non-elastic bracing member of the present invention is through a decrease in the circumference defined by the circumferentially spiraling bracing member about the limb. The dynamic decrease in circumference of the bracing member as axial rotation proceeds results in compression on the soft tissue of the limb and generates an active restraining force, thereby delimiting or actively resisting further axial rotation.

Thus, for example, each bracing member wound about the limb in one given direction will exert compressive restraining force as axial rotation occurs in the same direction as the winding direction of the bracing members. The present brace has the ability to respond to rotation about the joint by gradually and dynamically increasing compressive resistance as the degree of rotation about the joint increases, as well as gradually and dynamically reducing the compressive force as the degree of rotation decreases with a return to a normal, unrotated position. The brace is actively responding to rotation at all times.

Circumferentially- and spirally-binding the body on either side of the joint, as described, provides active resistance to axial rotation of the joint, as well as resistance to anterior tibial translation (i.e., anterior movement of the head of the tibia relative to the intercondylar surface of the femur), because of the substantially longitudinal inflexibility of the circumferentially-wound bracing member. The active resistance provided by the present derotation bracing apparatus may be selectively increased by detaching one end of a bracing member from the bracing member support, rotating the segment of the body engaged by the apparatus (e.g., the leg) and then re-securing the bracing member to the bracing member support. When the body segment (e.g., the leg) is brought back to its normal position following the rotation to tighten the tension (i.e., pre-tensioning the bracing device), the adjusted bracing member will tighten even more about the body to provide increased active resistance to axial rotation. This designed adjustability allows not only for selectively adjusting the functional resistance to rotation, but also provides for the accommodation of different limb dimensions among the normal population. Thus, the design provides a means for adjusting the tension in each of the bracing members, which affects the degree to which axial rotation about the joint is resisted.

In an improved embodiment of the invention described herein, the bracing members are configured with securement structures, for attaching the bracing members to a bracing member support, which effectively maximize the lateral vector forces and minimize the longitudinal vector forces imposed on the securement structures to help prevent the bracing members from pulling in a longitudinal direction on the terminal ends of the sleeve. As a result, when the bracing device has been pre-tensioned, as previously described, and the wearer rotates about the joint, the force exerted on the terminal ends of the bracing members is directed so that the terminal ends of the bracing members will not pull longitudinally on the terminal ends of the sleeve, thereby causing the sleeve to slip or roll down the limb.

In a further alternative embodiment of the invention disclosed herein, the same adjustment of the bracing members is achieved by structuring the bracing members with a length-adjusting device. In such an embodiment, the proximal and distal ends of each bracing member may be securely affixed to the bracing member support or may remain releasably attached to the bracing member support.

The bracing members are wrapped in both a clockwise (dextrorotary) and counterclockwise (levorotatory) direction about the body (e.g., the leg) in order to provide active resistance to rotation about the joint in the case of either internal or external tibial rotation. Internal tibial rotation may be described, for example, as rotating the body to the left while standing on the stationary left foot. However, depending on the specific functional imperative, the bracing members may be applied to circumferentially spiral in one direction only to address specific rotation-resistance requirements.

The present invention is directed to providing a new form of orthopedic brace which more effectively controls or delimits axial rotation in a physiological joint. Unlike prior examples of orthopedic braces, the present device is a flexible arrangement of bracing members which actively resist axial rotation in the joint by providing a flexible, circumferentially spiraling bracing device. A further consequence of this restrictive action is that translation in the joint is also delimited. The present invention effectively eliminates the rigid structural elements, as well as the mechanical hinge structures of previous orthopedic bracing systems, rendering it easy to use, comfortable to wear and suitable for use during normal everyday activity, including sporting activities. A further advantage of the present invention is the compressive force provided by the unique arrangement of circumferentially spiraling bracing members which provides proprioception to the wearer in increasing his awareness of the relationship of the target joint to the rest of his body thus enabling the wearer to recognize proper rotation and placement of the joint.

BRIEF DESCRIPTION OF THE SEVERAL VIEWS OF THE DRAWINGS

In the drawings, which illustrate what is currently considered to be the best mode for carrying out the invention:

FIG. 4 is a rear view in elevation of a human leg illustrating a third alternative embodiment of the orthopedic brace invention in place on the human leg;

FIG. 5 is a view in lateral cross section of the embodiment shown in FIG. 4, taken at line 5-5;

FIG. 12 is a plan view of an alternative embodiment of a single bracing member having a length-adjusting mechanism, the outer-facing surface of the bracing member being shown;

FIG. 13 is a plan view of the embodiment of a single bracing member shown in FIG. 12, the inner-facing surface of the bracing member being shown; and FIG. 14 is a longitudinal cross section of the embodiment shown in FIG. 12 taken at line 14-14 thereof.

DETAILED DESCRIPTION OF THE INVENTION

Figure 1:
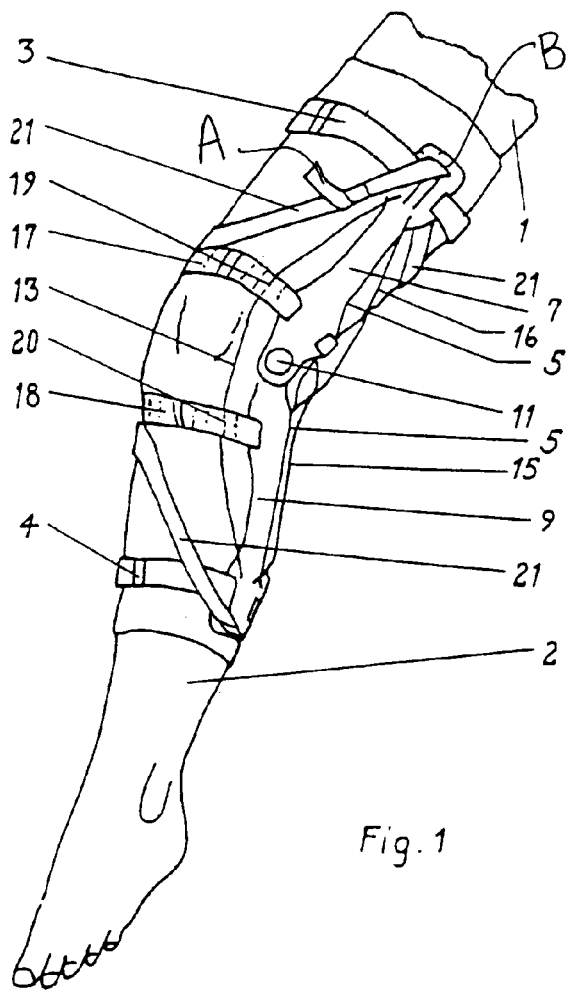
FIG. 1 is a front view in elevation of a human leg illustrating the essential elements of the orthopedic brace invention in place on the human leg, certain details being shown in phantom.

The principal elements of the orthopedic brace of the present invention are described fully in co-pending application Ser. No. 09/004,010, the contents of which are incorporated herein by reference. The following disclosure describes additional embodiments of the principal orthopedic brace invention and employs the same reference numerals used in Ser. No. 09/004,010.

As shown in FIG. 1, the orthopedic brace 20 of the present invention generally comprises a first bracing member support 32 for positioning about the leg 30, a second bracing member support 42 for positioning about the leg 30, and at least one circumferentially and spirally-wound bracing member 36 sized in length to extend between the first bracing member support 32 and the second bracing member support 42. Both the first bracing member support 32 and the second bracing member support 42 may generally be configured as a collar 26, which is sized to encircle the leg 30 at a given distance above or below the knee joint 22, depending on where a particular collar 26 is positioned for use.

As illustrated further in FIG. 1, the first bracing member support 32 and second bracing member support 42 serve as means for attachment of one or more spirally-wound bracing members 36 (only one being illustrated in FIG. 1). That is, the proximal end 38 of the bracing member 36 is secured to the first bracing member support 32 by a securement structure 60 which, as shown by way of example, may be a hook and loop-type tab 40 positioned on the bracing member 36 and a correspondingly interlockable portion 34 of hook and loop-type material positioned on or associated with the first bracing member support 32. Similarly, a securement structure 61 is associated with the second bracing member support 42 to fix the distal end 44 of the bracing member 36 thereto. The securement structure 61 shown in FIG. 1, by way of example only, is a hook and loop-type tab 48 attached to the distal end 44 of the bracing member 36 and a corresponding interlockable hook and loop-type portion 46 positioned on or associated with the second bracing member support 42. Many other suitable securement structure 60, 61 devices may be employed to secure the bracing member 36 to the first bracing member support 32 or second bracing member support 42 in an attached or detachable manner.

Figure 2:
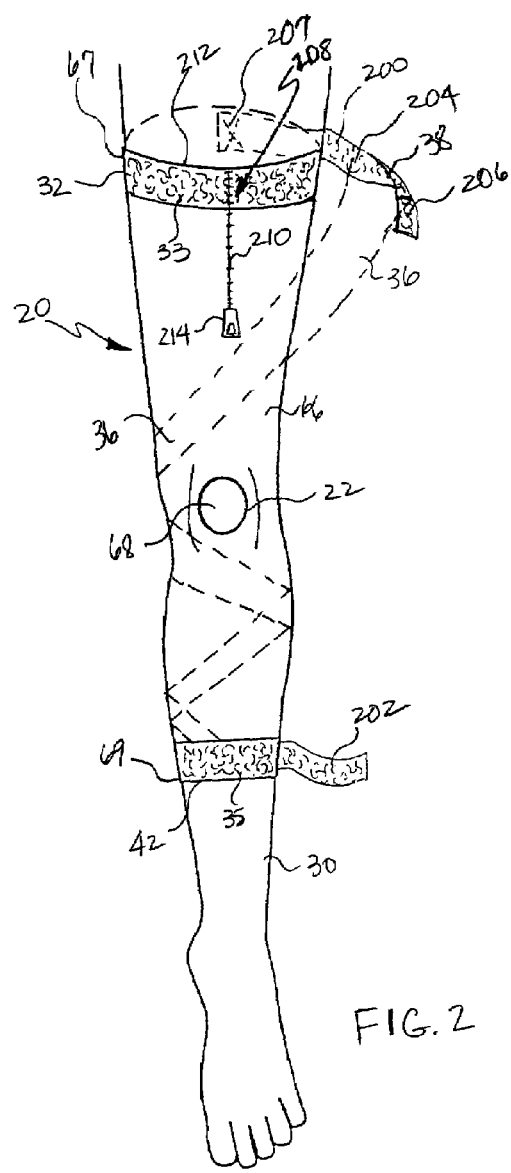
FIG. 2 is a front view in elevation of a human leg illustrating three alternative embodiments of the orthopedic brace invention in place on the human leg.

While the first bracing member support 32 and second bracing member support 42 may be separate, body-encircling bands as shown in FIG. 1, each may, in a first embodiment of the present disclosure, be incorporated into an undersleeve 66 as shown in FIG. 2. In this embodiment, the first bracing member support 32 and second bracing member support 42 are preferably formed of a material which has a lower coefficient of elasticity compared to the coefficient of elasticity of the undersleeve 66. As constructed, the undersleeve 66 is sized to extend from a distance above the knee 22 to a distance below the knee 22 and is sized to encircle the leg. The undersleeve 66, in general, serves as a support for the placement of one or more bracing members 36 (shown in phantom) about the leg 30 and helps keep the bracing members 36 in position about the leg 30. As previously described, the undersleeve 66 may even be constructed to incorporate one or more bracing members 36 into the fabric of the undersleeve 66, the bracing members 36 preferably being incorporated to wind in either direction (levorotatory and dextrorotatory) about the leg 30 to provide compression and derotation to the knee joint.

The undersleeve 66 of the present invention should be constructed in a manner which allows the undersleeve 66 to adapt to, or be accommodated on, virtually any size (i.e., circumferential dimension) of leg (or other limb or body part). The undersleeve 66 should also be constructed to remain statically in place about the leg or limb and not "ride down" or "ride up" the leg. Thus, FIG. 2 illustrates an embodiment of the orthopedic brace 20 where the lower coefficient of elasticity of both the first bracing member support 32 and the second bracing member support 42 provides greater contraction of the proximal end 67 and distal end 69, respectively, of the undersleeve 66 against the wearer's body, which assures that the undersleeve 66 will be properly fitted to the individual wearer's leg and that the undersleeve 66 will remain in place about the leg without riding or shifting down or up the leg 30. Notably, the first bracing member support 32 and second bracing member support 42 are configured with securement structures 60, 61 which enable the bracing members 36 to be secured to the undersleeve 66, as previously described. In FIG. 2, by way of example only, the first bracing member support 32 and second bracing member support 42 are shown as being made of a hook and loop-type material, although any other appropriate securement structure 60, 61 may be employed.

FIG. 2 also illustrates that a first stabilizing strap 200 and second stabilizing strap 202 may be attached to the first bracing member support 32 and second bracing member support 42, respectively, to enable the wearer to further decrease and then fix or substantially fix the circumference of the proximal end 67 and distal end 69 of the undersleeve 66 to adapt the orthopedic brace 20 to the circumference of the leg. The stabilizing straps 200, 202 fix or substantially fix the circumference of the undersleeve 66 about the limb which prevents the undersleeve 66 from rolling or shifting down the leg 30. The first stabilizing strap 200 may, as shown, be formed with a first surface 204 of hook and loop-type material which enables the first stabilizing strap 200 to be secured in place relative to and against the outer-facing surface 33 of the first bracing member support 32, which is also formed of hook and loop-type material. The outer-facing surface 206 of the first stabilizing strap 200 is likewise formed of hook and loop-type material so that the bracing member supports 36 are securable thereto in the manner previously described. The second stabilizing strap 202 is similarly constructed with hook and loop-type material to secure the second stabilizing strap 202 to the second bracing member support 42 and to accommodate attachment of bracing members 36 thereto. By way of example only, the first stabilizing strap 200 may be securely stitched (at 207) to the undersleeve 66; the second stabilizing strap 202 may be similarly attached. The stabilizing straps 200, 202 may preferably be inelastic, but may, in the alternative, be formed from an elastic material.

FIG. 2 also illustrates that the undersleeve 66 of the present invention may be structured with a closeable opening 208, shown here by way of example as a zipper 210, which extends from the proximal edge 212 of the undersleeve 66 to a distance away from the proximal edge 212 of the undersleeve 66. The closeable opening 208 provides for temporary expansion of the undersleeve 66 in a manner which allows the undersleeve 66 to be placed on the leg 30. A zipper is but one possible means of providing a closeable opening 208. In the conventional manner, the zipper 210 includes a closing mechanism 214 which allows the zipper 210 to be opened and closed. Because the undersleeve 66 is preferably constructed from material with a degree of elasticity which will ensure that the undersleeve 66 snugly conforms to the wearer's body, the zipper 210 facilitates placement of the undersleeve 66 on the wearer's leg.

Figure 3:
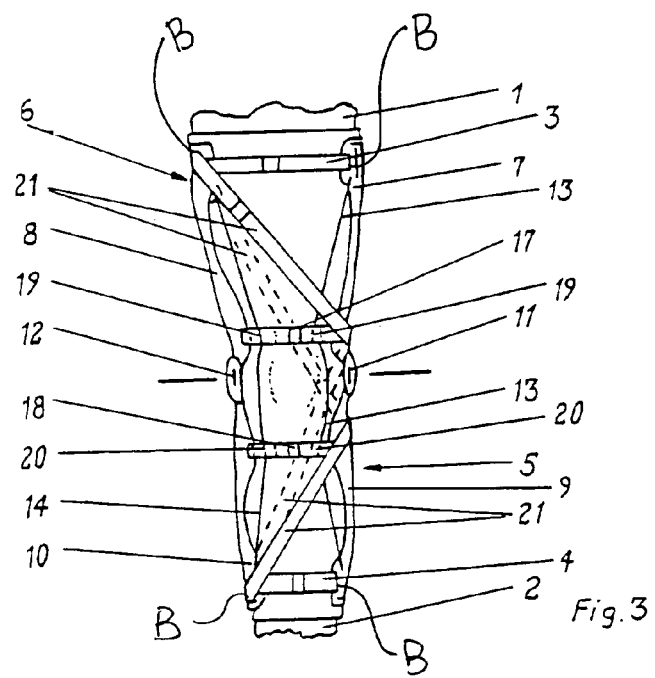
FIG. 3 is a front view in elevation of a human leg illustrating a second alternative embodiment of the orthopedic brace invention in place on the human leg.
Figure 3:
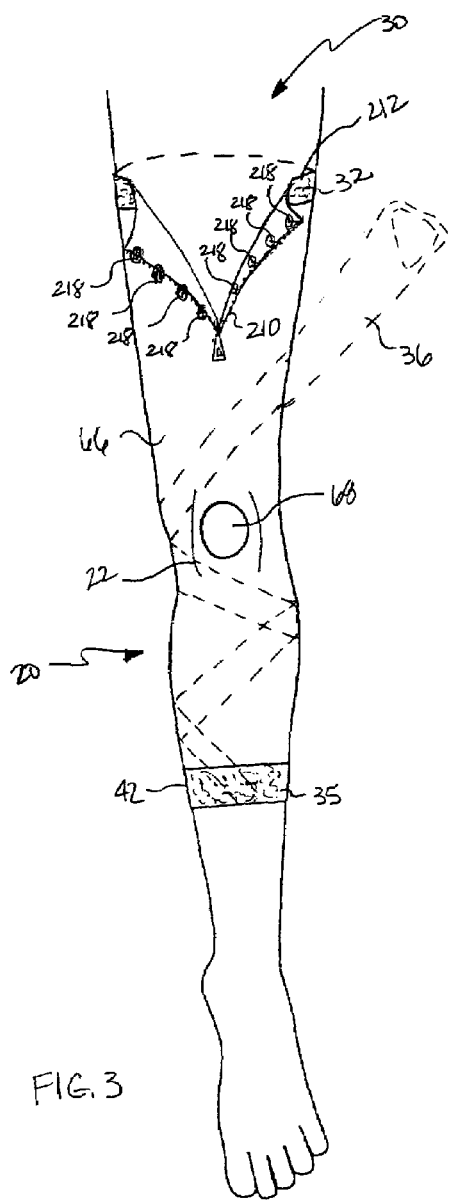

As further shown in FIG. 3, the undersleeve 66, when constructed with a zipper 210, may also include one or more connecting devices 218, such as hooks and eyes, snaps, hook and loop-type tabs or even lacing, which the wearer can use to bring the two sides of the zipper 210 in closer proximity to each other, thereby facilitating the closure of the zipper 210.

In yet another embodiment of the invention shown in FIG. 4, the undersleeve 66 may be configured with a proximal portion 220, positioned in proximity to the proximal edge 212 of the undersleeve 66, which has a lower coefficient of elasticity than the coefficient of elasticity of the undersleeve 66. The lower coefficient of elasticity of the proximal portion 220 serves to substantially fix the circumference of the undersleeve 66 to the circumference of the wearer's leg about the thigh and thereby stabilize the undersleeve 66 to prevent the proximal edge of the undersleeve 66 from slipping or rolling down the leg. The proximal portion may preferably be sized to partially encircle the circumference of the undersleeve 66 near the proximal edge 212 as shown, thereby providing an expansion gap 224, comprising an area of higher elasticity material of the undersleeve 66. The expansion gap 224 facilitates temporary expansion of the undersleeve 66 for placement about the leg 30. A stabilizing strap 226 may preferably be positioned in alignment with the proximal portion 220 to partially or fully encircle the circumference of the undersleeve 66 and to be positionable about the undersleeve 66 to span the expansion gap 224. The stabilizing strap 226 is configured with a closure mechanism 227 to secure the stabilizing strap 226 in position about the proximal portion 220 and is shown in FIG. 4, by way of example, as hook and loop-type material. The stabilizing strap 226 serves not only to reduce the circumference of the undersleeve 66 to fit the leg 30, but stabilizes the circumference of the undersleeve 66 so that the proximal edge 212 does not slip or roll down during use.

The proximal portion 220 may be positioned anywhere along the long axis of the undersleeve 66 in proximity to the proximal edge 212. The proximal portion 220 may even, in one embodiment, serve as the first bracing support member 32 by being formed with a securement structure 60 enabling attachment of the bracing members (not shown) thereto, as previously described. In an embodiment where the proximal portion 220 is positioned to serve as the first bracing member support 32, the stabilizing strap 226 is also preferably formed with a securement structure 60 to enable attachment of the bracing members thereto. As illustrated in FIG. 4, the securement structure 60 of the proximal portion 220 and stabilizing strap 226 may be hook and loop-type material as previously described. However, any other suitable securement structure 60 device may be employed to meet the requirements of the invention. When formed of hook and loop-type material, the stabilizing strap 226 may be rolled back upon itself and secured to the hook and loop material of the proximal portion 220 while donning the undersleeve 66, as shown in FIG. 5.

FIG. 4 shows, in phantom, that the undersleeve 66 may also be formed with a distal portion 228 comprised of material having a lower coefficient of elasticity than the coefficient of elasticity of the undersleeve 66. As described previously with respect to the proximal portion 220, the distal portion 228 may be sized to partially encircle the circumference of the undersleeve 66 near the distal edge 230 thereof to provide an expansion gap 232, and a stabilizing strap 234 may be provided to decrease and fix the circumference of the undersleeve 66 near the distal edge 230 thereof. The distal portion 228 may, as shown, also serve as the second bracing member support 42 and, as such, is structured with securement structures 61 to which the bracing members (not shown) may be attached. Further, the stabilizing strap 234 may also be structured with securement structures 61 to provide attachment of the bracing members thereto.

Both the proximal portion and distal portion of this embodiment may be integrally formed with the undersleeve 66 by unitary construction thereof or, in the alternative, may be applied to the undersleeve 66 as a separate element positioned on the outside surface of the sleeve, on the inside surface of the sleeve or incorporated into the length of the undersleeve 66. The coefficient of elasticity of one or both of the proximal portion 220 and distal portion 228 may be greater than or equal to zero.

As previously described in Ser. No. 09/004,010 and herein, the orthopedic brace of the present invention provides derotation of a joint, such as knee joint, by providing at least one circumferentially-spiraling bracing member which is spirally wound above and below the joint in a continuous, singular direction. The bracing members are held in circumferentially spiraling position about the joint by being attached to a first bracing member support and a second bracing member support. The invention provides derotation of the encircled joint by establishing a defined diameter for each bracing member, the diameter being adjustably fixed and defined by increasing or decreasing the circumferential distance between the proximal and =distal terminal ends of a bracing member in a process characterized as "pre-loading." Adjusting the defined diameter also provides selective compression of the joint by the bracing member or members. Thus, in the previously described embodiments of the invention, at least one terminal end of each bracing member is releasably attached to a respective bracing member support so that the distance between the terminal ends of the bracing member can be adjusted to pre-load the brace.

Figure 6:
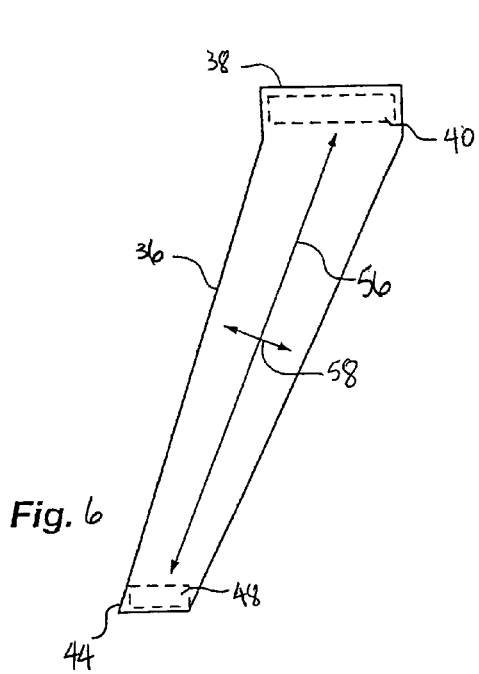
FIG. 6 is a plan view of an embodiment of a single bracing member, previously described in Ser. No. 09/004,010, which may be wound about the leg in a levorotatory direction, the outer-facing surface being shown (shown here for comparative purposes)
Figure 7:
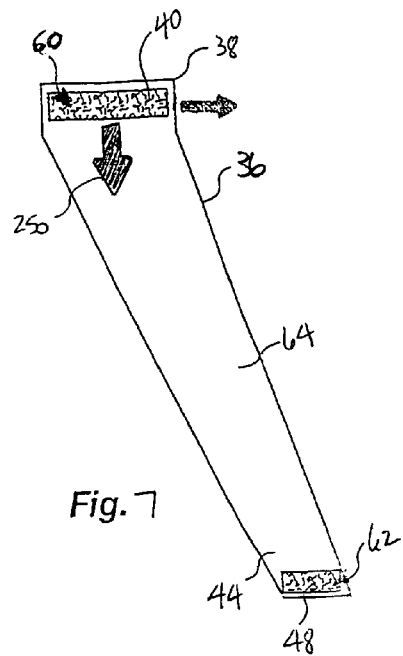
FIG. 7 is a plan view of the single bracing member shown in FIG. 6 with the inner-facing surface being shown.

FIGS. 6 and 7 illustrate a bracing member 36 previously described, comprising a length of material which has a longitudinal axis 56 formed through the length thereof. The material from which the bracing member 36 is made may be any suitable material which provides a certain flexibility to permit winding the bracing member 36 about the leg in a circumferentially-spiraling fashion as illustrated in FIG. 1. It is important, however, in the delimitation of the axial rotation about the joint that the bracing member 36 be substantially inelastic or non-extendible along the longitudinal axis 56 thereof. The material may also be substantially inelastic in a direction 58 normal to the longitudinal axis 56 of the bracing member 36; however, some elasticity in direction 58 may be beneficial in providing expandability of the bracing member 36 in response to muscle expansion and contraction during movement.

Figure 8:
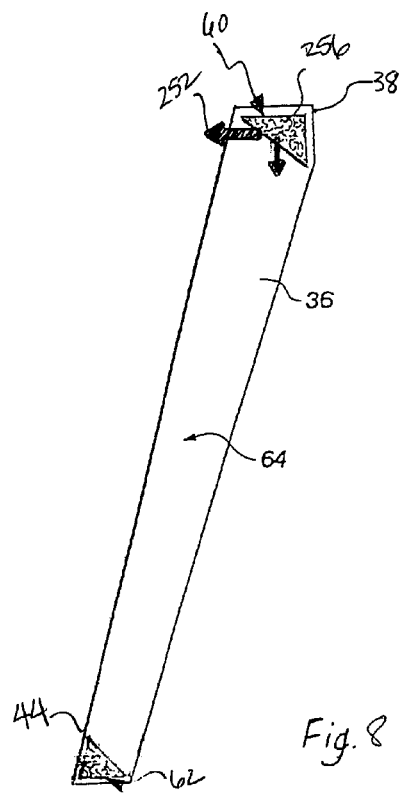
FIG. 8 is a plan view of a first alternative embodiment of a single bracing member, the inner-facing surface being shown.

The securement structure 60 positioned at the proximal end 38 of the bracing member 36 is shown in FIGS. 6 and 7 as a portion or tab 40 of hook and loop-type material, and the securement structure 62 positioned at the distal end 44 of the bracing member 36 is shown as a hook and loop-type tab 48. Both tab 40 and tab 48 have previously been described as being in the form of long strips oriented along the respective terminal ends of the bracing member 36. Elongated strips of hook and loop-type material, while effective to retain the bracing member 36 in secure engagement with the respective bracing member support, tend to contribute to a downward force on the bracing member 36, as suggested by the heavier arrow at 250, which may cause the bracing member 36 to likewise force the proximal edge of the undersleeve or the bracing member support to roll or slide down the wearer's leg when the joint is rotated. Therefore, in an alternative embodiment of the bracing member 36 shown in FIG. 8, the securement structure 60 located at the proximal end 38 of the bracing member 36 is especially shaped to maximize lateral vector forces on the hook and loop tab 256 to promote a sideward force, as suggested by the arrow at 252, rather than a downward force, thereby helping to keep the undersleeve or bracing member support in secure engagement about the wearer's leg (i.e., rather than rolling or slipping down the leg). The hook and loop tab 256 may, as shown, be generally triangular in shape to promote the described lateral vector forces and minimize downward vector forces. Similarly, the securement structure 62 at the distal end 44 of the bracing member 36 may also be shaped to maximize lateral vector forces and minimize upward vector forces to prevent the undersleeve or bracing member support from rolling or sliding up the leg.

Figure 9:
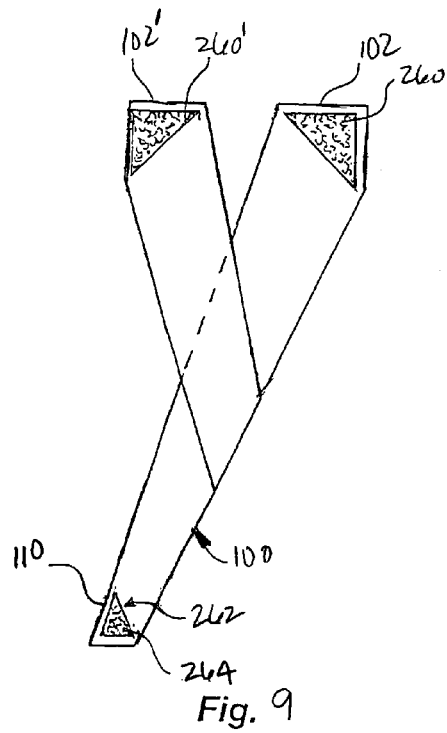
FIG. 9 is a plan view of a second embodiment of a double-ended bracing member, the inner-facing surface being shown.

By way of further example, the same especially-shaped securement structure may be adapted to a bracing member 100, as shown in FIG. 9, which is configured with two proximal ends 102, 102' for attachment to the first bracing member support (not shown). The securement structures 260, 260' may be generally triangular in shape to maximize lateral vector forces as described with respect to the single bracing member 36 shown in FIG. 8. Further, the securement structure 262 positioned at the distal end 110 of the bracing member 100 may be a triangularly-shaped hook and loop tab 264, or may be any other appropriate shape.

Figure 10:
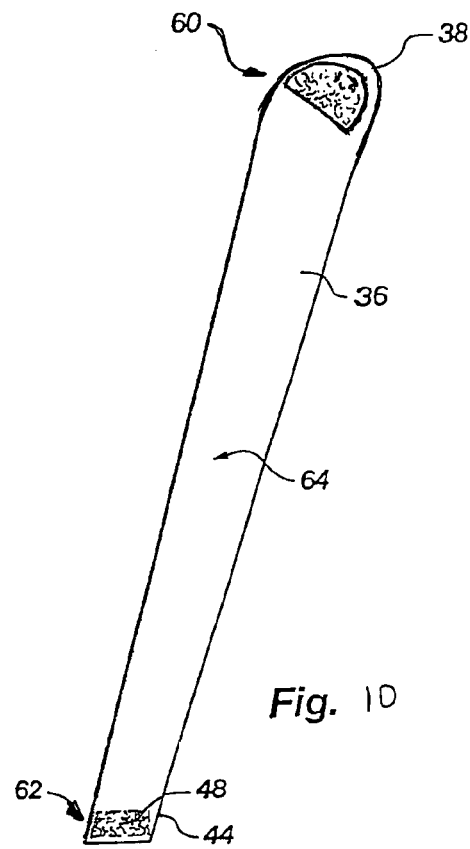
FIG. 10 is a plan view of a third alternative embodiment of a single bracing member, the inner-facing surface being shown.
Figure 11:
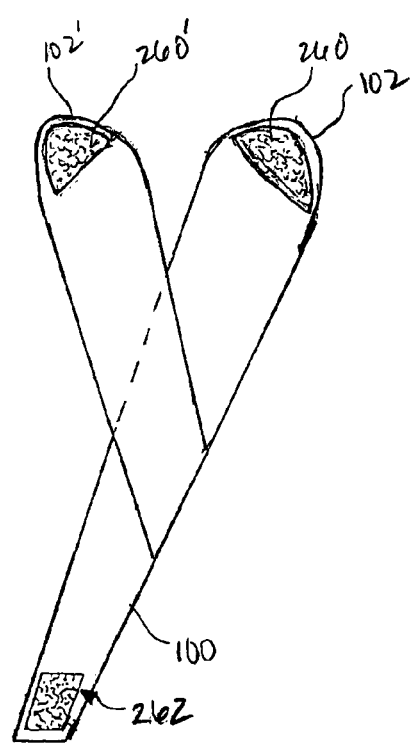
FIG. 11 is a plan view of a fourth embodiment of a double-ended bracing member, the inner-facing surface being shown.
Figure 1:
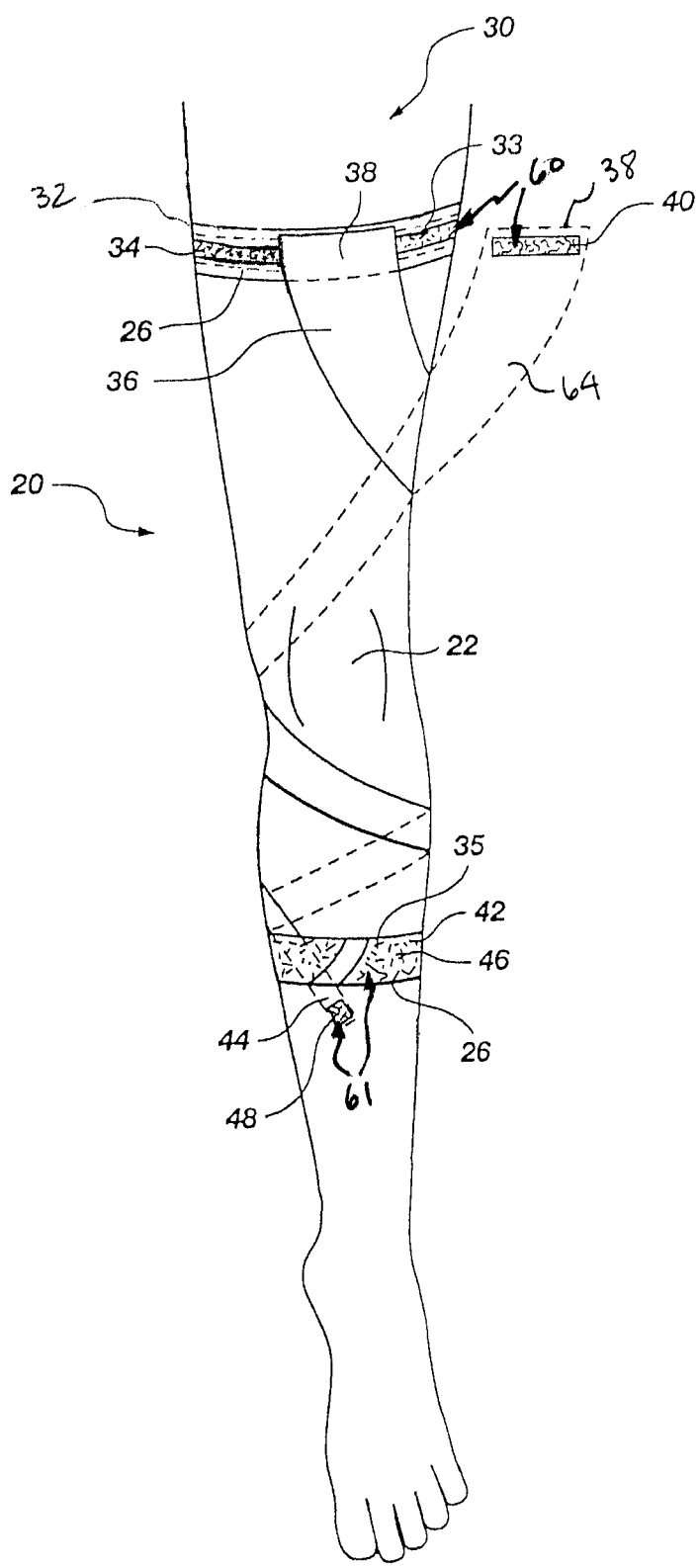

FIGS. 10 and 11 illustrate the same general principle with respect to the securement structure 60 or 260, 260' located at the proximal end 38 or 102, 102', respectively, of the bracing member 36 or 100, respectively, except that the securement structure 60 or 260, 260' can be modified in shape while still providing a maximization of lateral vector forces acting upon the securement structure 60 or 260, 260'. The securement structure 60 shown in FIG. 10 and the securement structures 260, 260' shown in FIG. 11 are, by way of example only, generally triangulate in shape, but have rounded corners. Other suitable shapes or dimensions may be employed in configuring the securement structures 60, 260, 260', and distal securement structures 62, 262, while still providing maximized lateral vector forces to promote lateral force rather than axial force (relative to the long axis of the limb) acting upon the securement structures.

The bracing member has been described herein, and in Ser. No. 09/004,010, as being structured to provide adjustability of the distance between the proximal end and distal end of the bracing member to thereby limit rotation of the joint from a defined plane of motion. That is, in the case of the knee joint, the normal plane of motion is defined by the plane of proper alignment of the femur with the tibia and fibula allowing for normal tension and flexion of the knee. The present invention acts to limit rotation of the femur out of the plane of motion with the tibia and fibula by establishing, within the plane of motion, a selected maximum distance between the proximal end and distal end of the bracing member. Once selected, an increase in distance between the proximal and distal ends of the bracing member caused by axial rotation of the joint out of the plane of motion will be effectively limited because the diameter defined by the circumferentially-spiraling bracing member will be decreased. That decrease in diameter of the circumferentially-spiraling bracing member results in compressive force on the soft tissue of the limb, providing resistance to rotation.

Heretofore, the bracing member has been described and illustrated as providing selected adjustability by having at least one terminal end configured with a releasable securement structure which allows the wearer to appropriately adjust and fix the distance between the proximal and distal ends of the bracing member within the defined plane of motion. However, the selected distance between the proximal end and distal end of the bracing member within the defined plane of motion may also be accomplished by adjustability of the length of the bracing member.

Thus, FIGS. 12-14 disclose, by way of example only, one means of providing adjustability of the length of the bracing member 36 as a method of establishing a selected distance between the proximal end 38 and distal end 44 of the bracing member 44 when circumferentially and spirally wound about a target joint. FIG. 12 shows an embodiment of a length-adjustable bracing member 36 where the bracing member 36 is comprised of a first bracing member portion 280 having a first end 282 and a second end 284, and a second bracing member portion 286, having a first end 288 (FIG. 13) and a second end 290. The first end 282 of the first bracing member portion 280 is the proximal end 38 of the bracing member 36 and the second end 290 of the second bracing member portion 286 is the distal end 44 of the bracing member 36. The bracing member 36 is illustrated as having a securement structure 60 positioned at the proximal end 38 thereof and a securement structure 62 positioned at the distal end 44 thereof. However, in an alternative embodiment, the proximal end 38 and distal end 44 of the bracing member 36 may be securely attached to the bracing support members.

The bracing member 36 is further configured with a length-adjusting device 292 which may be any device which adjusts the longitudinal distance between the proximal end 38 and distal end 44 of the bracing member 36. A very simplified device is illustrated in FIGS. 12-14 by way of example and comprises a first rod 296, a second rod 298 and a connecting bracket 300 to which each rod is journalled. The first end 288 of the second bracing member portion 286 is, as shown in FIG. 13, positioned about the second rod 298 and is secured in place on the inner-facing surface 64 of the bracing member 36 by such means as stitching 302. The second end 284 of the first bracing member portion 280 is positioned about the first rod 296 and is free to slide, in the direction of arrow 304 (FIG. 14), thereabout. The second end 284 is also formed with a releasable securement member 306 (shown in phantom in FIG. 12) which allows the second end 284 to be selectively secured to the outer-facing surface 308 of the first bracing member portion 280. When the orthopedic brace is in position about the leg, as previously described, and the proximal end 38 and distal end 44 of the bracing member are secured to the first bracing member support and second bracing member support, respectively, the wearer may selectively establish the distance between the proximal end 38 and distal end 44 of the bracing member within the defined plane of motion by axially rotating the leg inwardly (i.e., toward the center of the body), pulling on the second end 284 of the first bracing member portion 280 until a desired tautness or length in the bracing member 36 is achieved, securing the second end 284 in place against the outer-facing surface 308 of the bracing member 36 and rotating the leg outwardly again until the defined plane of rotation is established (i.e., the leg is in its normal position flexion of the knee). Any other suitable length-adjusting device or mechanism may be employed to accomplish the desired-function as described. Further, the length-adjusting device 292 may be located virtually anywhere along the entire length of the bracing member 36.

The embodiments of the invention described herein provide significant improvements in an orthopedic bracing system which provides active resistance to axial rotation about a joint. The embodiments of the invention illustrated herein are provided by way of example only and those skilled in the art will understand that variations and modifications of the embodiments illustrated herein may be made without departing from the present invention as defined by the claims. All such variations are intended to be within the scope of the present invention as defined in the claims.

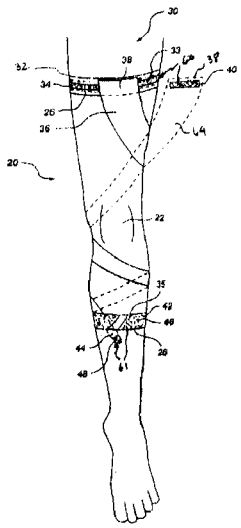

What is claimed is:

1. An orthopedic brace providing active resistance to axial rotation and translation in a joint comprising at least one circumferentially spiraling, length-adjustable, longitudinally inelastic bracing member having a proximal terminal end positioned on one side of a joint, a distal terminal end positioned on the other side of the joint along a longitudinal axis formed through the joint and a circumferentially spiraling distance extending between said proximal terminal end and said distal terminal end defining a circumference oriented about the joint from said proximal terminal end to said distal terminal end, active resistance to axial rotation and translation of the joint being provided by a change in said circumference responsive to a change in the position of said proximal terminal end relative to said distal terminal end, and being structured with a length adjustment device positioned between said proximal end and said terminal end of said at least one circumferentially spiraling bracing member to provide increased resistance to axial rotation and translation in the joint by selectively adjusting the length of said at least one circumferentially spiraling bracing member when said proximal end and said distal end are fixed in a selected position relative to each other.

2. The orthopedic brace of claim 1 further comprising a bracing member support, said proximal terminal end and said distal terminal end being attached to said bracing member support.

3. An orthopedic brace providing active resistance to axial rotation and translation in a joint comprising at least one circumferentially spiraling, length-adjustable, longitudinally inelastic bracing member having a proximal terminal end positioned on one side of a joint, a distal terminal end positioned on the other side of the joint along a longitudinal axis formed through the joint and a circumferentially spiraling distance extending between said proximal terminal end and said distal terminal end defining a circumference oriented about the joint from said proximal terminal end to said distal terminal end, said orthopedic brace further comprising a bracing member support comprising an undersleeve having a proximal edge and a distal edge, said proximal terminal end of said bracing member being attached near said proximal edge of said undersleeve and said distal terminal end of said bracing member being attached near said distal edge of said undersleeve; and
    wherein active resistance to axial rotation and translation of the joint being is provided by a change in said circumference responsive to a change in the position of said proximal terminal end relative to said distal terminal end.

4. An orthopedic brace providing active resistance to axial rotation and translation in a joint comprising:
    an undersleeve sized to encircle at least a portion of a wearer's body and to extend from one side of a joint to the other side of the joint, said undersleeve having a proximal edge positioned on one side of a joint and a distal edge positioned on the other side of the joint; and
    at least one circumferentially spiraling, longitudinally inelastic bracing member having a proximal end and a distal end attached to said undersleeve in proximity to said proximal edge of said undersleeve and said distal edge of said undersleeve, respectively, to define a circumferentially spiraling distance from said proximal end to said distal end thereof.

5. The orthopedic brace of claim 4 wherein said undersleeve is formed of a material having a coefficient of elasticity and wherein said undersleeve further comprises a proximal portion positioned near said proximal edge of said undersleeve, said proximal portion having a coefficient of elasticity lower than said coefficient of elasticity of said undersleeve.

6. The orthopedic brace of claim 5 wherein said proximal portion is sized to partially encircle said undersleeve and thereby provide an expansion gap comprising material having a greater coefficient of elasticity than said coefficient of elasticity of said proximal portion.

7. The orthopedic brace of claim 5 further comprising a first stabilizing strap positioned in alignment with said proximal portion to encircle at least a portion of said proximal portion.

8. The orthopedic brace of claim 5 wherein said undersleeve further comprises a distal portion positioned near said distal edge of said undersleeve, said distal portion having a coefficient of elasticity lower than said coefficient of elasticity of said undersleeve.

9. The orthopedic brace of claim 8 wherein said distal portion is sized to partially encircle said undersleeve and thereby provide an expansion gap comprising material having a greater coefficient of elasticity than said coefficient of elasticity of said distal portion.

10. The orthopedic brace of claim 9 further comprising a stabilizing strap positioned in alignment with said distal portion to encircle at least a portion of said distal portion.

11. The orthopedic brace of claim 8 wherein at least one of said proximal portion or said distal portion is positioned and configured to serve as a bracing member support for attachment of said at least one bracing member thereto.

12. The orthopedic brace of claim 4 wherein said undersleeve further comprises a closeable opening extending from said proximal edge of said undersleeve toward said distal edge thereof.

13. The orthopedic brace of claim 12 wherein said closeable opening is a zipper.

14. The orthopedic brace of claim 12 further comprising at least one connecting device attached to said undersleeve and positioned in proximity to said closeable opening.

15. The orthopedic brace of claim 12 further comprising a stabilizing strap connected to said undersleeve in proximity to said proximal edge of said undersleeve and oriented to be positionable over said closeable opening to substantially fix the circumference of said undersleeve.

16. The orthopedic brace of claim 15 wherein said undersleeve further comprises a closeable opening extending from said distal edge thereof and further comprising a stabilizing strap connected to said undersleeve in proximity to said distal edge of said undersleeve and oriented to be positionable over said closeable opening in said distal edge to substantially fix the circumference of said undersleeve.

17. A method of limiting axial rotation and translation in a joint comprising:
    providing an orthopedic brace configured to actively resist axial rotation and translation in a joint, said brace comprising a bracing member support and at least one circumferentially spiraling, length-adjustable bracing member attached to said bracing member support, said at least one circumferentially spiraling bracing member having a proximal end for positioning on one side of a joint, a distal end for positioning on the other side of the joint along a longitudinal axis formed through the joint and a circumferentially spiraling distance extending between said proximal end and said distal end defining a circumference oriented about the joint from said proximal end to said distal end, and having a length adjustment device positioned between said proximal end and said terminal end of said at least one circumferentially spiraling bracing member;
    positioning said orthopedic brace about a joint to extend said at least one bracing member from one side of the joint to the other side of the joint;
    establishing said circumferentially spiraling distance between said proximal end and said distal end of said bracing member to define a plane of motion;
    selectively increasing active resistance to axial rotation and translation in the joint by selectively adjusting said length adjustment device of said at least one circumferentially spiraling bracing member when said proximal end and said distal end are fixed relative to each other.

18. An orthopedic brace providing active resistance to axial rotation and translation in a joint comprising a bracing member support and at least one circumferentially spiraling, length-adjustable bracing member having a proximal end releasably attached to said bracing member support for positioning on one side of a joint, a distal end releasably attached to said bracing member support for positioning on the other side of the joint along a longitudinal axis formed through the joint and a circumferentially spiraling distance extending between said proximal end and said distal end defining a circumference oriented about the joint from said proximal end to said distal end, active resistance to axial rotation and translation of the joint being provided by a change in said circumference responsive to a change in the position of said proximal end relative to said distal end, and being structured with a length adjustment device positioned between said proximal end and said terminal end of said at least one circumferentially spiraling bracing member to provide increased resistance to axial rotation and translation in the joint by selectively adjusting the length of said at least one circumferentially spiraling bracing member when said proximal end and said distal end are fixed in a selected position relative to each other.

19. An orthopedic brace providing active resistance to axial rotation and translation in a joint comprising at least one circumferentially spiraling, length-adjustable, longitudinally inelastic bracing member, having a proximal end positioned on one side of a joint, a distal end positioned on the other side of the joint along a longitudinal axis formed through the joint and a circumferentially spiraling distance extending between said proximal end and said distal end defining a circumference oriented about the joint from said proximal end to said distal end, said at least one circumferentially spiraling bracing member being sized in length to spiral unidirectionally from one side of the joint to the other side of the joint, wherein active resistance to axial rotation and translation of the joint is initially provided by a change in said circumference responsive to a change in the position of said proximal end relative to said distal end of said circumferentially spiraling bracing member and said at least one circumferentially spiraling bracing member is structured with a length adjustment device positioned between said proximal end and said terminal end of said at least one circumferentially spiraling bracing member to provide increased resistance to axial rotation and translation in the joint by selectively adjusting the length of said at least one circumferentially spiraling bracing member when said proximal end and said distal end are fixed in a selected position relative to each other.

* * * * *

UNITED STATES PATENT AND TRADEMARK OFFICE
CERTIFICATE OF CORRECTION

| | | |
|---|---|---|
| PATENT NO. | : 7,473,236 B1 | |
| APPLICATION NO. | : 09/664462 | |
| DATED | : January 6, 2009 | |
| INVENTOR(S) | : Paul R. Mathewson | |

It is certified that error appears in the above-identified patent and that said Letters Patent is hereby corrected as shown below:

The Title Page, showing an illustrative Figure, should be deleted and substitute therefor the attached Title Page.

Delete Drawing Sheet 1, consisting of Fig. 1 and Fig. 3 and substitute therefor the Drawing Sheet consisting of Fig. 1, as shown on the attached page.

Signed and Sealed this

Seventh Day of September, 2010

David J. Kappos
*Director of the United States Patent and Trademark Office*

CERTIFICATE OF CORRECTION (continued)

(12) United States Patent  
Mathewson

(10) Patent No.: US 7,473,236 B1  
(45) Date of Patent: Jan. 6, 2009

(54) VARIABLY ADJUSTABLE BI-DIRECTIONAL DEROTATION BRACING SYSTEM

(76) Inventor: Paul R. Mathewson, 7726 N. Buckboard Dr., Park City, UT (US) 84098

( * ) Notice: Subject to any disclaimer, the term of this patent is extended or adjusted under 35 U.S.C. 154(b) by 1826 days.

(21) Appl. No.: 09/664,462

(22) Filed: Sep. 18, 2000

Related U.S. Application Data

(63) Continuation-in-part of application No. 09/004,010, filed on Jan. 7, 1998, now Pat. No. 6,142,965.

(60) Provisional application No. 60/039,104, filed on Feb. 25, 1997.

(51) Int. Cl.  
*A61F 13/00* (2006.01)

(52) U.S. Cl. .................... 602/62; 602/23; 602/26; 602/60

(58) Field of Classification Search ........... 602/60–65, 602/20, 23, 26  
See application file for complete search history.

(56) References Cited

U.S. PATENT DOCUMENTS

| | | |
|---|---|---|
| 366,590 A | 7/1887 | Lubin |
| 967,585 A | 8/1910 | Teufel |
| 2,574,873 A | 11/1951 | Jobst |
| 2,646,796 A | 7/1953 | Scholl |
| 3,306,288 A | 2/1967 | Rosenfield |
| 3,307,546 A | 3/1967 | Cherio et al. |
| 3,419,003 A | 12/1968 | Krauss et al. |
| 3,504,672 A | 4/1970 | Moon |
| 3,529,601 A | 9/1970 | Kirkland |
| 3,680,549 A | 8/1972 | Lehneis et al. |
| 3,724,457 A | 4/1973 | Klatte |
| 3,805,781 A * | 4/1974 | Hoey ..................... 602/75 |
| 3,831,467 A | 8/1974 | Moore |
| 3,900,199 A | 8/1975 | McGonagle |
| 4,201,203 A | 5/1980 | Applegate |
| 4,269,181 A | 5/1981 | Delannoy |
| 4,353,362 A | 10/1982 | DeMarco |
| 4,378,009 A | 3/1983 | Rowley et al. |
| 4,425,912 A | 1/1984 | Harper |
| 4,503,846 A | 3/1985 | Martin |
| 4,697,583 A | 10/1987 | Mason et al. |
| 4,733,656 A | 3/1988 | Marquette |
| 4,802,466 A | 2/1989 | Meyers et al. |
| 4,941,462 A * | 7/1990 | Lindberg ..................... 602/16 |
| 4,986,264 A | 1/1991 | Miller |

(Continued)

FOREIGN PATENT DOCUMENTS

DE 4013693 A1 * 8/1991

(Continued)

Primary Examiner—Michael Brown  
(74) Attorney, Agent, or Firm—Morriss O'Bryant Compagni

(57) ABSTRACT

A lightweight orthopedic brace having no rigid structural elements is constructed from flexible material and is designed primarily to provide for restriction of rotational movement and translation about the target joint by providing flexible bracing members which wind in a circumferentially spiraling manner about a target joint to provide active resistance to axial rotation and translation in the joint. The embodiments of the invention disclosed here provide improved means for placing the invention on the body about a joint, improved means for attachment of bracing members to bracing member supports and improved means for adjusting the length of bracing member to selectively provide for restriction of rotational movement about the target joint.

19 Claims, 6 Drawing Sheets